(12) United States Patent
Xiao et al.

(10) Patent No.: US 7,964,714 B2
(45) Date of Patent: Jun. 21, 2011

(54) GENE EXPRESSION SUPPRESSION AGENTS

(75) Inventors: Yingxian Xiao, Potomac, MD (US);
Xin-Hua Feng, Houston, TX (US)

(73) Assignee: Potomac Pharmaceuticals Inc.,
Potomac, MD (US)

( * ) Notice: Subject to any disclaimer, the term of this patent is extended or adjusted under 35 U.S.C. 154(b) by 770 days.

(21) Appl. No.: 10/552,909

(22) PCT Filed: May 12, 2003

(86) PCT No.: PCT/US03/14631
§ 371 (c)(1),
(2), (4) Date: Oct. 13, 2005

(87) PCT Pub. No.: WO2004/106488
PCT Pub. Date: Dec. 9, 2004

(65) Prior Publication Data
US 2007/0105795 A1     May 10, 2007

(51) Int. Cl.
| C12Q 1/68 | (2006.01) |
| C12P 19/34 | (2006.01) |
| C12N 15/00 | (2006.01) |
| C07H 21/02 | (2006.01) |
| C07H 21/04 | (2006.01) |

(52) U.S. Cl. ....... 536/24.1; 435/6; 435/91.1; 435/91.31; 435/320.1; 536/23.1; 536/24.5

(58) Field of Classification Search ............. 435/6, 91.1, 435/91.31, 320.1; 514/44; 536/23.1, 24, 536/24.1, 24.5
See application file for complete search history.

(56) References Cited

U.S. PATENT DOCUMENTS

| 5,580,761 | A | 12/1996 | Greatbatch et al. |
| 5,610,015 | A | 3/1997 | Wickens et al. |
| 5,624,803 | A | 4/1997 | Noonberg et al. |
| 5,677,131 | A | 10/1997 | Wickens et al. |
| 5,683,902 | A | 11/1997 | Hampel et al. |
| 5,723,323 | A | 3/1998 | Kauffman et al. |
| 5,750,667 | A | 5/1998 | Wickens et al. |
| 5,763,192 | A | 6/1998 | Kauffman et al. |
| 5,807,743 | A | 9/1998 | Stinchcomb et al. |
| 5,814,476 | A | 9/1998 | Kauffman et al. |
| 5,817,483 | A | 10/1998 | Kauffman et al. |
| 5,824,514 | A | 10/1998 | Kauffman et al. |
| 5,837,503 | A | 11/1998 | Doglio et al. |
| 5,840,555 | A | 11/1998 | Oshima et al. |
| 5,869,248 | A | 2/1999 | Yuan et al. |
| 5,877,162 | A | 3/1999 | Werner et al. |
| 5,902,880 | A * | 5/1999 | Thompson ................... 536/24.5 |
| 5,976,862 | A | 11/1999 | Kauffman et al. |
| 5,994,526 | A | 11/1999 | Meulewaeter et al. |
| 5,998,193 | A | 12/1999 | Keese et al. |
| 6,025,192 | A | 2/2000 | Beach et al. |
| 6,033,856 | A | 3/2000 | Koerner et al. |
| 6,057,153 | A | 5/2000 | George et al. |
| 6,057,156 | A | 5/2000 | Akhtar et al. |
| 6,074,836 | A | 6/2000 | Bordignon et al. |
| 6,080,575 | A | 6/2000 | Heidtmann et al. |
| 6,103,890 | A | 8/2000 | Jarvis et al. |
| 6,107,078 | A | 8/2000 | Keese et al. |
| 6,127,173 | A | 10/2000 | Eckstein et al. |
| 6,146,886 | A | 11/2000 | Thompson |
| 6,183,959 | B1 | 2/2001 | Thompson |
| 6,255,071 | B1 | 7/2001 | Beach et al. |
| 6,280,936 | B1 | 8/2001 | Burgin et al. |
| 6,294,711 | B1 | 9/2001 | Meulewaeter et al. |
| 6,300,131 | B1 | 10/2001 | Greider et al. |
| 6,326,193 | B1 | 12/2001 | Liu et al. |
| 6,346,398 | B1 | 2/2002 | Pavco et al. |
| 6,380,170 | B1 | 4/2002 | Muller et al. |
| 6,506,559 | B1 * | 1/2003 | Fire et al. ........................ 435/6 |
| 2003/0084471 | A1 * | 5/2003 | Beach et al. .................. 800/278 |
| 2005/0014263 | A1 * | 1/2005 | Moyer et al. .................. 435/456 |
| 2006/0122381 | A1 * | 6/2006 | Streb et al. .................... 536/23.7 |

FOREIGN PATENT DOCUMENTS

| WO | WO 01/92513 A1 | 12/2001 |
| WO | WO 02/44321 | * 6/2002 |

OTHER PUBLICATIONS

Jennings, P.A. et al., EMBO J., vol. 6, No. 10, pp. 3043-3047 (1987).*
Hallenberg et al., Biochimica et Biophysica Acta, vol. 91565, pp. 169-173 (2001).*
Paule et al., Nucleic Acids Res., vol. 28, No. 6, pp. 1283-1298 (2000).*
Willis, I. M.., Eur. J. Biochem., vol. 212, pp. 1-11 (1993).*
Bitko et al., "Phenotypic silencing of cytoplasmic genes . . . ," BMC Microbiology, 2001, 17 pages, 1: 34, Mobile, Alabama, USA.
Kuwabara et al., "A Novel Allosterically trans-Activated . . . ," Molecular Cell, 1998, pp. 617-627, vol. 2, Tokyo, Japan.
Wong-Staal, "Ribozyme gene therapy for HIV infection," Advanced Drug Delivery Reviews 17, 1995, pp. 363-368, San Diego, CA, USA.
Caplen et al., "Specific inhibition of gene expression by small . . . ," PNAS, 2001, pp. 9742-9747, vol. 98, No. 17, Baltimore, Maryland, USA.
Sui et al., "A DNA vector-based RNAi technology . . . ," PNAS, 2002, pp. 5515-5520, vol. 99, No. 8, Boston, MA, USA.
Yu et al., "RNA interference by expression of . . . ," PNAS, 2002, pp. 6047-6052, vol. 99, No. 9, Ann Arbor, MI, USA.
Brummelkamp et al., "A System for Stable Expression . . . ", Science Magazine, 2002, pp. 550-553, vol. 296.
Lee et al., "Expression of small interfering RNAs targeted . . . ", Nature Biotechnology, 2002, pp. 500-505, vol. 20.

* cited by examiner

*Primary Examiner* — Jane Zara
(74) *Attorney, Agent, or Firm* — Shook, Hardy & Bacon LLP

(57) ABSTRACT

A method is provided for making gene suppression agents to be used in eukaryotic cells by using a recombinant DNA construct containing at least one transcriptional unit compromising a transcriptional promoter, a template sequence for making a RNA molecule, and a transcriptional terminator. Mechanisms of the RNA mediated gene suppression include, but are not limited to, RNA interferences (RNAi). The use of the agents as tools for biomedical research as well as medicinal products is also disclosed.

21 Claims, 3 Drawing Sheets

SEQUENCE LISTING

```
<160> NUMBER OF SEQ ID NOS: 9

<210> SEQ ID NO 1
<211> LENGTH: 27
<212> TYPE: DNA
<213> ORGANISM: Human
<220> FEATURE:
<221> NAME/KEY: primer_bind
<223> OTHER INFORMATION: Primer to amplify upstream promoter containing
      Box D in the Human 5S RNA gene
<300> PUBLICATION INFORMATION:
<310> PATENT DOCUMENT NUMBER: PCT WO 2004/106488 A2
<311> PATENT FILING DATE: 2003-05-12
<312> PUBLICATION DATE: 2004-12-09

<400> SEQUENCE: 1
aacggatcca aaacgctgcc tccgcga                                       27

<210> SEQ ID NO 2
<211> LENGTH: 25
<212> TYPE: DNA
<213> ORGANISM: Human
<220> FEATURE:
<221> NAME/KEY: primer_bind
<223> OTHER INFORMATION: Downstream reverse primer used to amplify the
```

-continued upstream promoter containing Box D in the Human 5S RNA gene. The
sequence contains a PstI site at 7 bp upstream of the
transcription site.

<400> SEQUENCE: 2
tagacgctgc aggaggcgcc tggct                                        25

<210> SEQ ID NO 3
<211> LENGTH: 269
<212> TYPE: DNA
<213> ORGANISM: Human
<220> FEATURE:
<221> NAME/KEY: promoter
<223> OTHER INFORMATION: Calculated BamHI-PstI fragment of the upstream
      promoter containing Box D in the Human 5S gene. Cloned into
      pBluescript-KS to give plasmid pPPVI.

<400> SEQUENCE: 3
ggatccaaaa cgctgcctcc gcgacagggc ggaggacgga gggcgtccca ggatcgtggg    60
ccctgggcct gacgcctcgg agcactccct gctccgagcg ggcccgatgt ggtggaagct   120
cgggagcgcg ggagccgggg gaaggccgcg ggcagccgtc gggggtcccc gatccgagcc   180
ccgcggcccc gggctggcgg tgtcggctgc aatccggcgg gcacggccgg ccgggctggg   240
ctcttggggc agccaggcgc ctccttcag                                    269

<210> SEQ ID NO 4
<211> LENGTH: 84
<212> TYPE: DNA
<213> ORGANISM: Human
<220> FEATURE:
<221> NAME/KEY: terminator
<223> OTHER INFORMATION: Comprises Box A, C and terminator of the human
      5S RNA gene.  Serves as a top strand to anneal with SEQ ID NO: 5
      to create a double-stranded DNA molecule.

<400> SEQUENCE: 4
agaagacgaa gctaagcagg gtcgggcctg gttagtactt ggatgggaga ccgcctggga    60
ataccgggtg ctgtaggctt tttg                                          84

<210> SEQ ID NO 5
<211> LENGTH: 88
<212> TYPE: DNA
<213> ORGANISM: Human
<220> FEATURE:
<221> NAME/KEY: terminator
<223> OTHER INFORMATION: Comprises Box A, C and terminator of the human
      5S RNA gene.  Serves as a top strand to anneal with SEQ ID NO: 4
      to create a double-stranded DNA molecule.

<400> SEQUENCE: 5
tcgacaaaaa gcctacagca cccggtattc ccaggcggtc tcccatccaa gtactaacca    60
ggcccgaccc tgcttagctt cgtcttct                                      88

<210> SEQ ID NO 6
<211> LENGTH: 367
<212> TYPE: DNA
<213> ORGANISM: Human
<220> FEATURE:
<221> NAME/KEY: promoter
<223> OTHER INFORMATION: A BamHI-SalI fragment of plasmid pPPV2
      containing the upstream promoter containing Box D, A, C and the
      terminator of the Human 5S gene.

<400> SEQUENCE: 6
ggatccaaaa cgctgcctcc gcgacagggc ggaggacgga gggcgtccca ggatcgtggg    60

-continued

```
ccctgggcct gacgcctcgg agcactccct gctccgagcg ggcccgatgt ggtggaagct    120
cgggagcgcg ggagccgggg gaaggccgcg ggcagccgtc gggggtcccc gatccgagcc    180
ccgcggcccc gggctggcgg tgtcggctgc aatccggcgg gcacggccgg ccgggctggg    240
ctcttggggc agccaggcgc ctccttcagg aattcgatag aagacgaagc taagcagggt    300
cgggcctggt tagtacttgg atgggagacc gcctgggaat accgggtgctg taggcttttt    360 tgtcgac                                                              367
```

<210> SEQ ID NO 7
<211> LENGTH: 51
<212> TYPE: DNA
<213> ORGANISM: Human
<220> FEATURE:
<221> NAME/KEY: misc_RNA
<222> LOCATION: Positioned with PstI at the 5' end and BbsI at the 3' end.
<223> OTHER INFORMATION: Contains designed siRNA sequence. Serves as a top strand to anneal with SEQ ID NO: 8 to create a double-stranded DNA molecule. The "n" bases represent any of the a, g, c, or t bases.

<400> SEQUENCE: 7

```
gcnnnnnnnn nnnnnnnnnn ntttcggnnn nnnnnnnnnn nnnnnntttt t             51
```

<210> SEQ ID NO 8
<211> LENGTH: 59
<212> TYPE: DNA
<213> ORGANISM: Human
<220> FEATURE:
<221> NAME/KEY: misc_RNA
<222> LOCATION: Positioned with PstI at the 5' end and BbsI at the 3' end.
<223> OTHER INFORMATION: Contains designed siRNA sequence. Serves as a top strand to anneal with SEQ ID NO: 7 to create a double-stranded DNA molecule. The "n" bases represent any of the a, g, c, or t bases.

<400> SEQUENCE: 8

```
agctaaaaan nnnnnnnnnn nnnnnnnncc gaaannnnnn nnnnnnnnnn nnngctgca     59
```

<210> SEQ ID NO 9
<211> LENGTH: 399
<212> TYPE: DNA
<213> ORGANISM: Human
<220> FEATURE:
<221> NAME/KEY: misc_structure
<222> LOCATION: A BamHI-SalI fragment of plasmid pPPV2 containing the siRNA design.
<223> OTHER INFORMATION: The second stretch of the 19 "n" bases are complementary and reverse to the first stretch. The "n" bases represent any of the a, g, c, or t bases.

<400> SEQUENCE: 9

```
ggatccaaaa cgctgcctcc gcgacagggc ggaggacgga gggcgtccca ggatcgtggg    60
ccctgggcct gacgcctcgg agcactccct gctccgagcg ggcccgatgt ggtggaagct    120
cgggagcgcg ggagccgggg gaaggccgcg ggcagccgtc gggggtcccc gatccgagcc    180
ccgcggcccc gggctggcgg tgtcggctgc aatccggcgg gcacggccgg ccgggctggg    240
ctcttggggc agccaggcgc ctccttcagc nnnnnnnnnn nnnnnnnnnt tcggnnnnn     300 nnnnnnnnnn nnnnttttta gctaagcagg gtcgggcctg gttagtactt ggatgggaga    360
ccgcctggga ataccgggtg ctgtaggctt tttgtcgac                           399
```

GENE EXPRESSION SUPPRESSION AGENTS

RELATED APPLICATION

This application claims the benefit of priority of provisional application No. 60/377,964 filed May 7, 2002.

BACKGROUND OF THE INVENTION

1. Technical Field

The present invention relates to medicine and biomedical research. More specifically, the present invention relates to expression systems to produce small hairpin RNAs (shRNAs) or interfering RNAs (siRNAs), collectively called siRNA in this application, in eukaryotic cells and methods for expressing siRNAs in eukaryotic cells. The present invention also relates to the use of the expression systems as medicinal products.

2. Related Art

RNA interference (RNAi) is a process of sequence-specific, post-transcriptional gene silencing (PTGS) in animals and plants initiated by double-stranded RNA (dsRNA) that is homologous to the silenced gene. It is an evolutionarily conserved phenomenon and a multi-step process that involves generations of active siRNAs in vivo through the action of a mechanism that is not fully understood. RNAi has been used as a reverse genetic tool to study gene function in multiple model organisms, such as plants, *Caenorhabditis elegants* and *Drosophila*, where large dsRNAs efficiently induce gene-specific silencing. In mammalian cells dsRNAs, 30 base pairs or longer, can activate antiviral response, leading to the non-specific degradation of RNA transcripts and to a general shutdown of host cell protein translation. As a result, the long dsRNA is not a general method for silencing specific genes in mammalian cells. Recently, various siRNAs that were synthesized chemically or generated biologically using DNA templates and RNA polymerases have been used to down regulate expression of targeted genes in cultured mammalian cells. Among approaches used, it is highly desirable to use DNA constructs that contain promoters of transcriptions and templates for siRNAs to generate siRNAs in vivo and in vitro. Though several different promoters have been adapted in such DNA constructs, types of promoters used remain limited to, Type III RNA polymerase III (Pol III) promoters, such as the U6 promoter and the H1 promoter, and promoters that require viral RNA polymerases, such as the T7 promoter. The present invention provides methods and designs to produce gene expression suppression agents that greatly expand potential usages of siRNAs.

SUMMARY OF THE INVENTION

The present invention relates to methods to produce gene expression suppression agents for expression of siRNAs in mammalian cells. Such agents contain RNA polymerase III (Pol III) transcription promoter elements, template sequences for siRNAs, which are to be transcribed in host cells, and a terminator sequence.

The promoter is any native or engineered transcription promoter. As examples of such promoters (not intended on being limiting), in one embodiment, the promoter is a Type I Pol III promoter, while in another embodiment, the promoter is a combination of Type I Pol III promoter elements and Type III Pol III promoter elements. In other embodiments other types of promoters are present.

The targeted region of siRNA is anywhere on a transcript of any sequence in eukaryotic or viral genomes. The terminator is any native or engineered sequence that terminates the transcription by Pol III or other types of RNA polymerases.

Such gene expression suppression agents are delivered into eukaryotic cells, including (but not limited to) mammals, insects, worms and plants, with any routes, procedures or methods, such as (but not limited to), in vivo, in vitro, ex vivo, electroporations, transfections or viral vector transduction.

BRIEF DESCRIPTION OF THE FIGURES

FIG. 1 is a schematic representation of a strategy for generating siRNA in mammalian cells using vertebrate Type I Pol III promoters (5S rRNA gene promoter and others). "A Box", "C Box", "D Box" and "IE" are Pol III promoter elements, "+1" is an initiation site of transcription, "Tn" is a termination site of the Pol III promoter transcript, and the arrow indicates the orientation of transcription. The siRNA template consists of sense, spacer, antisense and terminator sequences, and generates a hairpin dsRNA when expressed. "Sense" is a 17-23 nucleotide (nt) sense sequence that is identical to that of the target gene and is a template of one strand of the stem in the hairpin dsRNA. "Spacer" is a 4-15 nt sequence and is a template of the loop of the strand of the stem in the hairpin dsRNA. "Terminator" is the transcriptional termination signal of five thymidines (5 Ts).

DETAILED DESCRIPTION OF THE INVENTION

Figure 1:
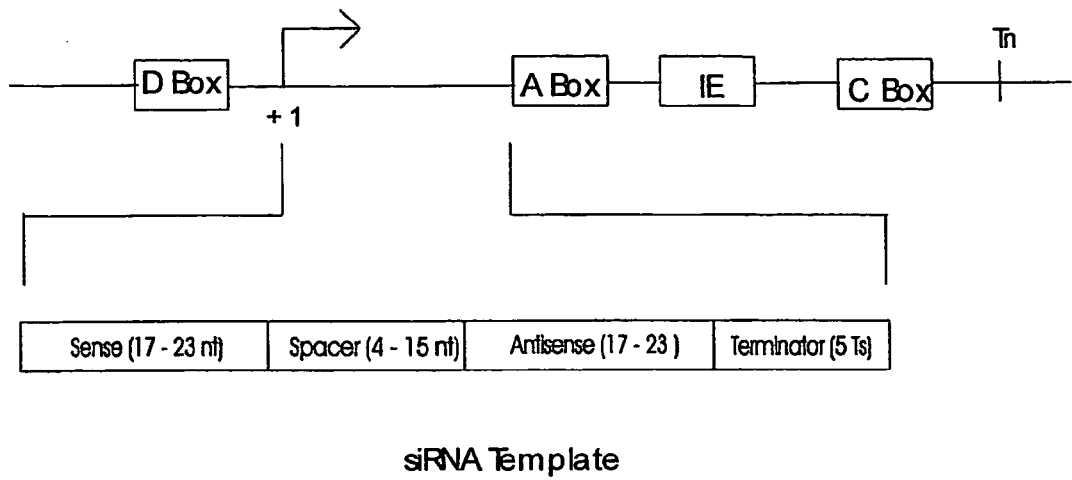
FIG. 1 is a schematic representation of the embodiment for generating siRNA in mammalian cells using vertebrate Type I Pol III promoters. Specifically.
Figure 2:
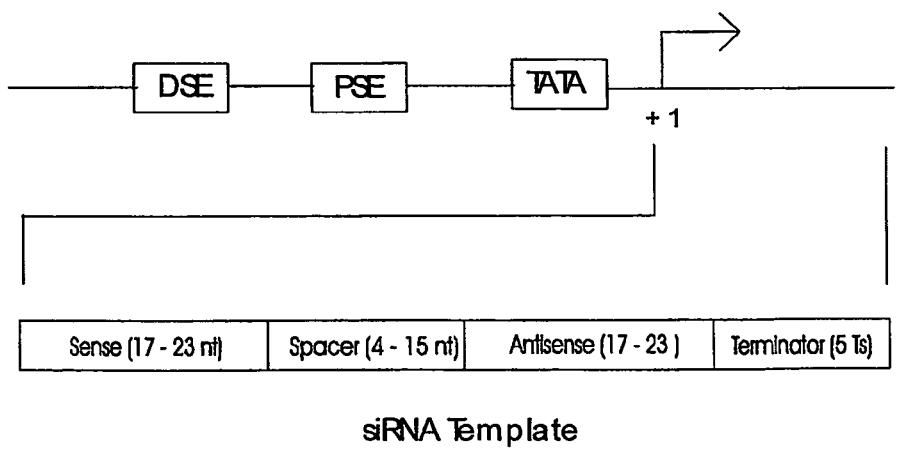
FIG. 2 is a schematic representation of the embodiment for generating siRNA in mammalian cells using vertebrate Type III Pol III promoters (U6 gene promoter, H1 RNA gene promoter, Y1 gene promoter, Y3 gene promoter, RNase P gene promoter and others). DSE, distal sequence element of Pol III promoter: PSE, proximal sequence element of Pol III promoter; TATA, a promoter element; +1, initiation site of transcription; the arrow indicates the orientation of transcription; siRNA Template, a 43-66 nt engineered insert that is the template for generating a hairpin dsRNA against a target gene; Sense, a 17-23 nt sense sequence from the target gene, template of one strand of stem in the hairpin; Spacer, a 4-15 nt sequence, template of loop of the hairpin; Antisense, a 17-23 nt antisense sequence, template of the other strand of stem in hairpin; Terminator, the transcriptional termination signal of 5 thymidines (5 Ts).
Figure 3:
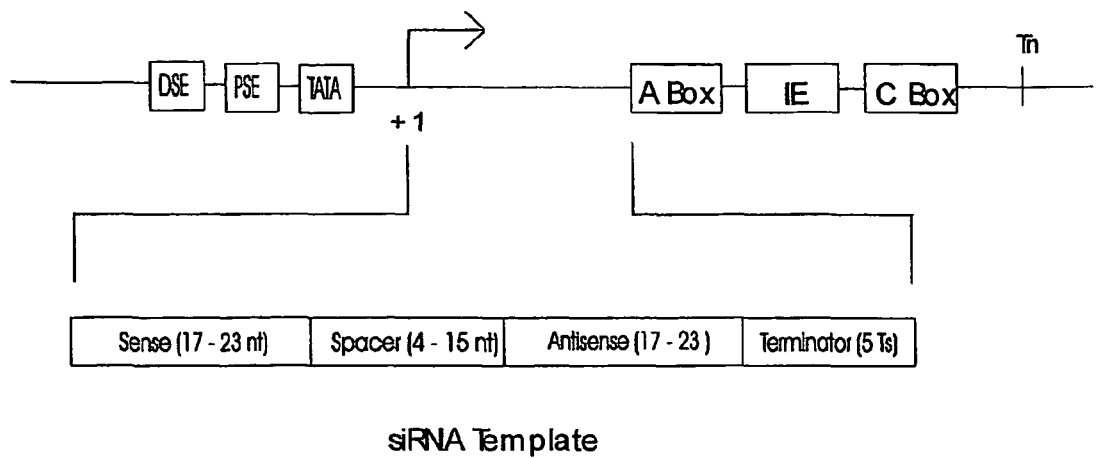
FIG. 3 is a schematic representation of the embodiment for generating siRNA in mammalian cells using an engineered Pol III promoter containing the elements in both Type I and Type III promoters. "DSE" is a distal sequence element of Type III Pol III promoter. "PSE" is a proximal sequence element of Type III Pol III promoter, "TATA" is a Type III Pol III promoter element. "A Box," "C Box" and "IE" are Type I Pol III promoter elements. "+1" is an initiation site of transcription. "Tn" is a termination site of the Type III Pol III promoter transcript. The arrow indicates the orientation of transcription. The siRNA template consists of sense, spacer, antisense and terminator sequences, and generates a hairpin dsRNA when expressed. "Sense" is a 17-23 nt sense sequence that is identical to that of the target gene and is a template of one strand of the stem in the hairpin dsRNA. "Spacer" is a 4-15 nt sequence and is a template of the loop of the hairpin dsRNA. "Antisense" is a 17-23 nt antisense sequence and is a template of the other strand of stem in hairpin dsRNA. "Terminator" is the transcriptional termination signal of five thymidines (5 Ts).
Figure 4:
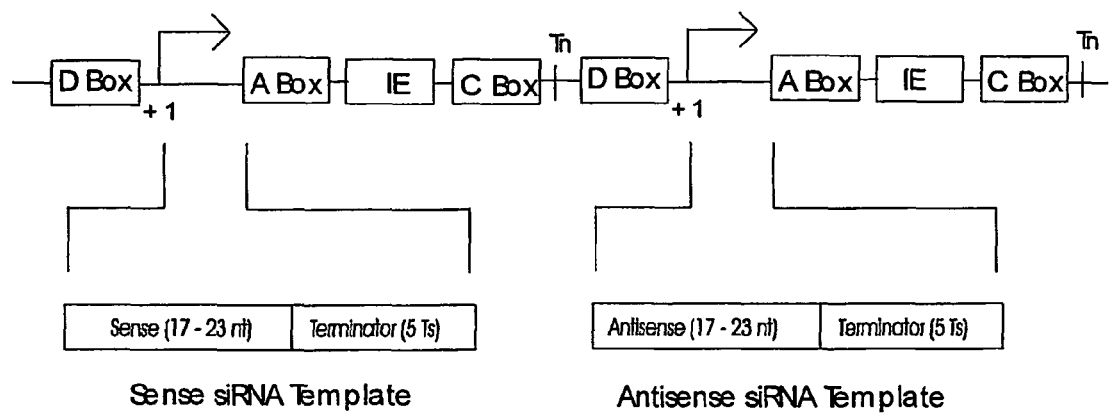
FIG. 4 is a schematic representation of the embodiment for generating siRNA in mammalian cells using two vertebrate Type I Pol III promoters that drive transcriptions of sense siRNA and antisense siRNA separately. "A Box", "C Box", "D Box" and "IE" are Pol III promoter elements. "+1" is an initiation site of transcription. "Tn" is a termination site of the Pol III promoter transcript. The arrow indicates the orientation of transcription. "Sense siRNA Template" is a 22-28 nt engineered insert that is the template for generating a sense single-stranded RNA (ssRNA) against a target gene, and consists of sense and terminator sequences. "Antisense siRNA Template" is a 22-28 nt engineered insert that is the template for generating an antisense ssRNA against a target gene, and consists of antisense and terminator sequences. "Sense" is a 17-23 nt sense sequence that is identical to that of the target gene and is a template of one strand of the stem in the hairpin dsRNA. "Spacer" is a 4-15 nt sequence and is a template of loop of hairpin dsRNA. "Antisense" is a 17-23 nt antisense sequence and is a template of the other strand of the stem in the hairpin dsRNA. "Terminator" is the transcriptional termination signal of five thymidines (5 Ts).
Figure 5:
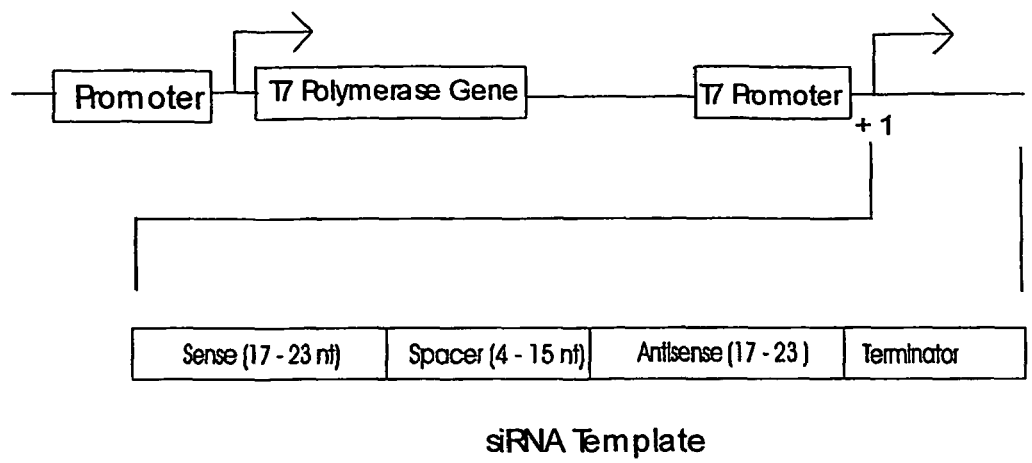
FIG. 5 is a schematic representation of the embodiment for generating siRNA in mammalian cells using an engineered T7 polymerase and T7 promoter. "Promoter" is a constitutive or context-dependent promoter such as an inducible promoter or a cell type specific promoter; "T7 Polymerase Gene" is a sequence coding for T7 polymerase. T7 promoter is a T7 promoter. "+1" is an initiation site of transcription. The arrow indicates the orientation of transcription. The siRNA template consists of sense, spacer, antisense and terminator sequences, and generates a hairpin dsRNA when expressed. "Sense" is a 17-23 nt sense sequence that is identical to that of the target gene and is a template of one strand of the stem in the hairpin dsRNA. "Spacer" is a 4-15 nt sequence and is a template of the loop of the hairpin dsRNA. "Antisense" is a 17-23 nt antisense sequence and is a template of the other strand of stem in the hairpin dsRNA. "Terminator" is an engineered terminator for T7 polymerase.
Figure 6:
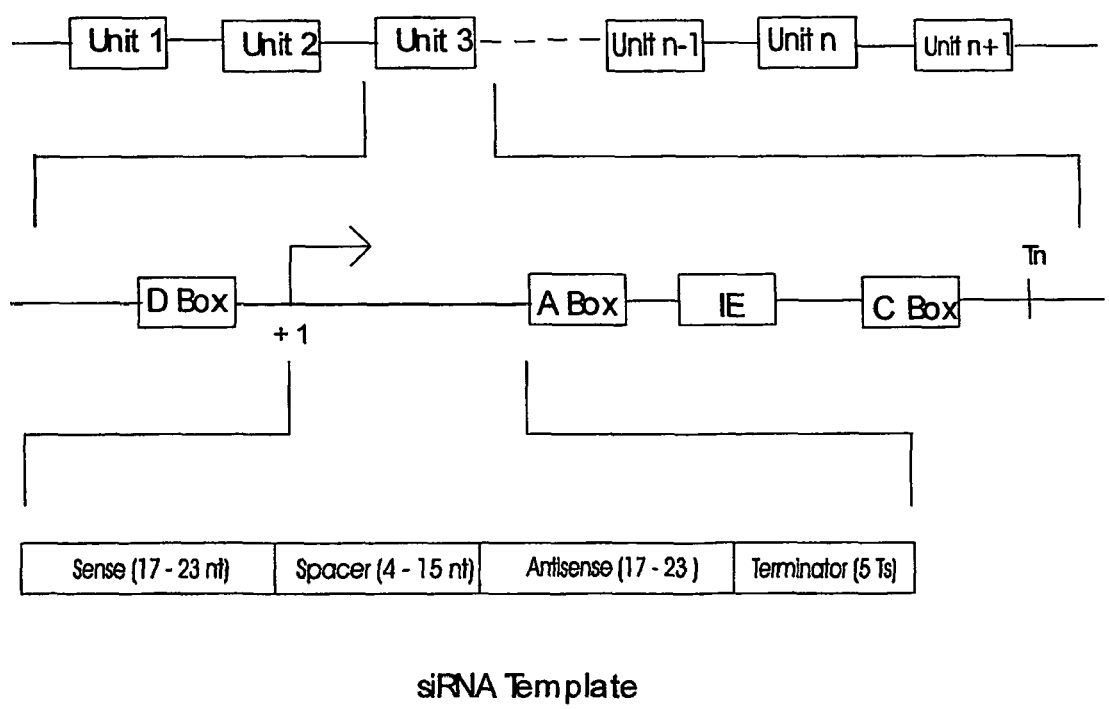
FIG. 6 is a schematic representation of the embodiment for generating multiple siRNAs in mammalian cells using a single multiple transcription unit construct. "Unit" is a transcription unit that contains a vertebrate Type I Pol III promoter and a siRNA template. "A Box", "C Box", "D Box" and "IE" are Pol III promoter elements. "+1" is an initiation site of transcription. "Tn" is a termination site of the Pol III promoter transcript. The arrow indicates the orientation of transcription. The structure of siRNA template consists of sense, spacer, antisense and terminator sequences, and is an engineered insert that is the template for generating a hairpin dsRNA against a target gene. "Sense" is a 17-23 nucleotide (nt) sense sequence that is identical to that of the target gene and is a template of one strand of the stem in the hairpin dsRNA. "Spacer" is a 4-15 nt sequence and is a template of the loop of the hairpin dsRNA. "Antisense" is a 17-23 nt antisense sequence and is a template of the other strand of stem in hairpin dsRNA. "Terminator" is the transcriptional termination signal of five thymidines (5 Ts). The multiple siRNAs may target a single region on one gene, different regions on one gene, or one region on each of many genes.

The following detailed description is provided to aid those skilled in the art to use the present invention. It should not be viewed as defining limitations of this invention. The present invention is directed to selectively suppress expression of genes targeted within mammalian cells by making and using DNA constructs that contains RNA polymerase III (Pol III) transcription promoter elements, template sequences for siRNAs, which are to be transcribed in host cells, and a terminator sequence. The promoter is any native or engineered transcription promoter. In one embodiment, the promoter is a Type I Pol III promoter. The essential elements of Type I promoter, such as "A Box", "C Box", "D Box" and "IE" are included in the DNA construct. In this embodiment, siRNA template is arranged between the "D Box" and "A Box". In another embodiment, the promoter is a combination of Type I Pol III promoter elements and Type III Pol III promoter elements. In this embodiment, the essential elements of both types of promoters, such "A Box", "C Box", and "IE" of Type I promoter, as well as "DSE", "PSE" and "TATA" of Type III promoter are included in the DNA construct, with "DSE", "PSE" and "TATA" in the upstream region of "+1" position, "A Box", "C Box", and "IE" in the down stream region of the "+1" position. Any promoter that is functioned in the mammalian cells is suitable to be used in this invention. Modifications, such as adding inducible or enhancing elements to exiting promoters, is suitable to be used in this invention.

The targeted region of siRNA is anywhere on a transcript of any sequence in mammalian or viral genomes. In some embodiments, templates for siRNA code for RNA molecules with "hairpin" structures contains both sense and antisense sequences of targeted genes. In other embodiments, the template for sense sequence and the template for antisense sequences are driven by different promoters.

The terminator is any native or engineered sequence that terminates the transcription by Pol III or other types of RNA polymerases, such as, but without being limited to, a stretch of 4 or more thymidines (T) residues in a DNA molecule.

Any transcriptional unit containing a promoter, a template for RNA and a terminator, is suitable to be constructed with one other unit, or multiple units, in a DNA molecule as an agent. In one embodiment, a multiple units construct is showed. More than one kind of the gene expression suppression agents (DNA molecules) are suitable to be introduced into mammalian cells together. The siRNAs generated within the same mammalian cell by these multiple units or co-introduction approaches provide agents ability to target one specific region in one targeted RNA molecule, multiple regions in one targeted RNA molecule, or multiple regions in more than one RNA molecules.

Such DNA constructs as indicated above can be constructed as a part of any suitable cloning vectors or expression vectors. Then the agents can be delivered into cells, tissues or organisms with any routes, procedures or methods, such as in vivo, in vitro, ex vivo, injection, electroporations, transfections or viral vector transduction.

EXAMPLES

Example 1

Cloning of the Human 5S rDNA Regulatory Sequences

The promoter chosen for the experimental design proposed below is the human 5S rRNA gene. The sequence is available in the database: Genbank Accession Number X12811. 5S rRNA promoter contains downstream Boxes A and C and upstream Box D. In FIG. 1, the 49 nt sequence between the initiation site of the 5S rRNA and Box A is proposed to be replaced with interfering RNA sequence. Generation of a cassette containing both upstream and downstream boxes will be carried out in two steps. Cloning of the Box A and C can be achieved by chemical synthesis. The upstream Box D is done by PCR.

Cloning of the recombinant 5S rDNA Box D is carried out through PCR using forward primer (AACggatccaaacgctgcctccgcga) (Seq. 1) and reverse primer (TAGACGCTGCAG-GAGGCGCCTGGCT) (Seq. 2), which can then be subcloned into BamHI and PstI sites of pBS2SK. The Box A/C can be synthesized as top strand (AGAAGACGAagctaagcagggtcgggcctggttagtacttggatgggagaccgcctgggaataccggg tgctgtaggcttttg) (Seq. 3) and bottom strand (TCGA-CAAAAAGCCTACAGCACCCGGTATTC-CCAGGCGGTTCTCCCATCCAA GTACTAACCAGGC-CCGACCCTGCTTAGCTTCGTCTTCT) (Seq. 4), which are then annealed and subloned into EcoRFV and SalI sites downstream of the cloned Box D. The annealed DNA fragment is engineered with a BbsI site.

Example 2

Insertion and Cloning of RNAi Sequence

The RNAi cassette will be synthesized as two strands and cloned between PstI and BbsI sites. The RNAi cassette is designed as follows:

```
                                              (Seq. 5)
5' GC(N19)TTTCGG(61N)TTTTT 3'

(Seq. 6)
3' ACGTCG(61N)AAAGCC(N19)AAAAATCGA 5'
```

N19 is the 19 nt target DNA sequence selected from the transcribed region of a target gene. 61N is the reverse and complementary strand of N19. Transcription is initiated from the first base of N19 target sequence and terminated at the poly T.

Example 3

Targeting ErbB2/Her2 in Breast Cancers

ErbB2/Her2 gene is amplified in about 30% of breast cancers in humans, causing fast growth and metastasis of cancer cells. Herceptin, an antibody made by Genentech that blocks ErbB2 functions, is the only agent used by ErbB2-positive breast cancer patients that slows progression of metastatic breast disease and increases overall survival for patients given the drug along with standard chemotherapy compared to chemotherapy alone. Generation of siRNAs targeting ErbB2 developed with this invention should provide an alternative treatment.

Example 4

Targeting BCR-Abl tyrosine kinase in chronic myelogenous leukemia (CML) and other cancers. BCR-Abl is a fusion gene product that frequently occurs in CML. STI571, also called Gleevec developed by Novartis, is a newly approved anticancer agent to target BCR-Abl in CML. Generation of siRNAs against the fusion gene BCR-Abl, without interfering with the normal expression of either BCR or Abl gene, developed with this invention should have great potential for gene therapy to treat CML.

Example 5

Targeting Hepatitis B Virus (HBV)

Using this invention to target different sites of the HBV genome will provide a potent gene therapy to treat hepatitis B infected patients.

Example 6

Targeting Human Immunodeficiency Virus Type 1 (HIV-1)

Using this invention to target different sites of the HIV genome will provide a potent gene therapy for HIV infected patients. A multiple units agent simultaneously targeting multiple sites, such as env, gag, pol, vif, nef, vpr, vpu and tat, may be suitable to address resistances resulted from mutations of the HIV genome.

---

We claim:

1. A recombinant DNA construct containing at least one transcriptional unit comprising a transcriptional promoter, a template sequence for making an RNA molecule, and a transcriptional terminator, said transcriptional promoter being selected from the group consisting of Type I Pol III promoter and a promoter containing one or more essential elements of a Type I Pol III promoter, said one or more essential elements including, from 5' to 3', a D Box, an A Box, an Intermediate Element, and a C Box, said template sequence being an oligonucleotide positioned between said D Box and said A Box, said oligonucleotide excluding 5 Ts.

2. The construct of claim 1, wherein said Type I Pol III promoter is a native Type I Pol III promoter.

3. The construct of claim 1, wherein said Type I Pol III promoter is an engineered Type I Pol III promoter.

4. The construct of claim 1, wherein said promoter containing one or more essential elements of the Type I Pol III promoter is a native promoter containing one or more essential elements of the Type I Pol III promoter.

5. The construct of claim 1, wherein said promoter containing one or more essential elements of the Type I Pol III promoter is an engineered promoter containing one or more essential elements of the Type I Pol III promoter.

6. A cloning expression vector that contains the construct of claim 1.

7. The construct of claim 1 wherein said template sequence includes a terminator sequence.

8. The construct of claim 1 wherein said terminator sequence is a transcriptional termination signal consisting of 5 thymidines.

9. The construct of claim 1 wherein said template sequence further includes a spacer of 4-15 thymidines.

10. The construct of claim 1, wherein said oligonucleotide comprises a sense sequence, a spacer, an antisense sequence, and a terminator.

11. The construct of claim 10, wherein said sense sequence comprises 17-23 nucleotides.

12. The construct of claim 10, wherein said spacer comprises 4-15 nucleotides.

13. The construct of claim 10, wherein said antisense sequence comprises 17-23 nucleotides.

14. The construct of claim 10, wherein said terminator comprises 5 thymidines.

15. The construct of claim 1, wherein said promoter includes a first D Box, A Box, Intermediate Element, and C Box, and a second D Box, A Box, Intermediate Element and C Box, and said oligonucleotide comprises a sense template positioned between said first D box and first A Box and an antisense template positioned between said second D Box and second A Box.

16. The construct of claim 15 wherein said sense template includes a sense sequence and a terminator sequence.

17. The construct of claim 16 wherein said sense sequence comprises 17-23 nucleotides.

18. The construct of claim 16 wherein said terminator comprises 5 thymidines.

19. The construct of claim 15 wherein said antisense template includes an antisense sequence and a terminator sequence.

20. The construct of claim 19 wherein said antisense sequence comprises 17-23 nucleotides.

21. The construct of claim 19 wherein said terminator comprises 5 thymidines.

* * * * *